US008663311B2

(12) United States Patent
Besselink et al.

(10) Patent No.: US 8,663,311 B2
(45) Date of Patent: Mar. 4, 2014

(54) DEVICE COMPRISING BIODEGRADABLE BISTABLE OR MULTISTABLE CELLS AND METHODS OF USE

(75) Inventors: Petrus Antonius Besselink, AT Enschede (NL); Travis Yribarren, San Mateo, CA (US); Randolf Von Oepen, Los Altos, CA (US)

(73) Assignee: CeloNova Stent, Inc., San Antonio, TX (US)

( * ) Notice: Subject to any disclaimer, the term of this patent is extended or adjusted under 35 U.S.C. 154(b) by 1204 days.

(21) Appl. No.: 11/317,495

(22) Filed: Dec. 22, 2005

(65) Prior Publication Data

US 2006/0241739 A1    Oct. 26, 2006

Related U.S. Application Data

(63) Continuation-in-part of application No. 10/270,771, filed on Oct. 11, 2002, which is a continuation of application No. 09/012,843, filed on Jan. 23, 1998, now Pat. No. 6,488,702.

(60) Provisional application No. 60/036,359, filed on Jan. 24, 1997.

(51) Int. Cl.
*A61F 2/06* (2013.01)
(52) U.S. Cl.
USPC .......................................... 623/1.15; 623/1.17
(58) Field of Classification Search
USPC ............. 623/1.11, 1.15, 1.17, 1.12, 1.3, 1.18, 623/1.19, 1.2
See application file for complete search history.

(56) References Cited

U.S. PATENT DOCUMENTS

| 3,069,125 | A |   | 12/1962 | Hewitt, Jr. |         |
|-----------|---|---|---------|-------------|---------|
| 3,508,587 | A |   | 4/1970  | Mauch       |         |
| 3,657,744 | A |   | 4/1972  | Ersek       |         |
| 3,898,717 | A |   | 8/1975  | Schwartz    |         |
| 4,665,906 | A |   | 5/1987  | Jervis      |         |
| 4,733,665 | A | * | 3/1988  | Palmaz      | 606/108 |
| 4,739,762 | A |   | 4/1988  | Palmaz      |         |
| 4,886,062 | A |   | 12/1989 | Wilktor     |         |
| 4,969,890 | A |   | 11/1990 | Sugita et al. |       |
| 4,990,155 | A | * | 2/1991  | Wilkoff     | 606/191 |

(Continued)

FOREIGN PATENT DOCUMENTS

| DE | 8812719     | 11/1989 |
|----|-------------|---------|
| EP | 0 274 846 A1 | 7/1988 |

(Continued)

OTHER PUBLICATIONS

U.S. Appl. No. 10/270,771 and its prosecution history including the Office Actions/Advisory Actions mailed Jul. 27, 2006 and Jul. 29, 2003 and the Amendments filed Jan. 26, 2007, Mar. 9, 2004 and Sep. 15, 2003.

(Continued)

*Primary Examiner* — Thomas McEvoy
(74) *Attorney, Agent, or Firm* — Novak Druce Connolly Bove + Quigg LLP

(57) ABSTRACT

Expandable biodegradable devices formed of bistable and multistable unit cells for use in devices, such as stents and graft systems, are provided, in which the device has two or more stable configurations, including a contracted configuration and an expanded configuration, the contracted stable configuration having a smaller diameter than the expanded configuration.

30 Claims, 7 Drawing Sheets

(56) References Cited

U.S. PATENT DOCUMENTS

| | | | |
|---|---|---|---|
| 4,994,071 A | | 2/1991 | MacGregor |
| 5,102,417 A | | 4/1992 | Palmaz |
| 5,104,404 A | | 4/1992 | Wolff |
| 5,141,360 A | | 8/1992 | Zeman |
| 5,147,370 A | | 9/1992 | McNamara |
| 5,192,307 A | | 3/1993 | Wall |
| 5,197,978 A | * | 3/1993 | Hess ............................ 623/1.18 |
| 5,226,913 A | | 7/1993 | Pinchuk |
| 5,234,448 A | | 8/1993 | Wholey et al. |
| 5,282,823 A | | 2/1994 | Schwartz et al. |
| 5,354,308 A | * | 10/1994 | Simon et al. ................. 623/1.15 |
| 5,383,892 A | | 1/1995 | Cardon et al. |
| 5,383,926 A | | 1/1995 | Lock et al. |
| 5,397,355 A | | 3/1995 | Marin et al. |
| 5,403,341 A | | 4/1995 | Solar |
| 5,411,507 A | | 5/1995 | Heckele |
| 5,419,760 A | * | 5/1995 | Narciso, Jr. ........................ 604/8 |
| 5,449,373 A | * | 9/1995 | Pinchasik et al. ............. 606/198 |
| 5,449,382 A | | 9/1995 | Dayton |
| 5,496,365 A | | 3/1996 | Sgro |
| 5,500,013 A | * | 3/1996 | Buscemi et al. ............. 623/1.22 |
| 5,545,208 A | | 8/1996 | Wolff et al. |
| 5,545,210 A | | 8/1996 | Hess et al. |
| 5,556,413 A | | 9/1996 | Lam |
| 5,562,690 A | | 10/1996 | Green et al. |
| 5,601,593 A | | 2/1997 | Freitag |
| 5,643,314 A | | 7/1997 | Carpenter et al. |
| 5,670,161 A | * | 9/1997 | Healy et al. .................. 623/1.42 |
| 5,695,516 A | | 12/1997 | Fischell et al. |
| 5,702,419 A | * | 12/1997 | Berry et al. .................. 623/1.13 |
| 5,725,570 A | * | 3/1998 | Heath ............................ 623/1.2 |
| 5,733,303 A | | 3/1998 | Israel et al. |
| 5,755,774 A | | 5/1998 | Pinchuk |
| 5,755,776 A | | 5/1998 | Al-Saadon |
| 5,776,181 A | * | 7/1998 | Lee et al. ..................... 623/1.15 |
| 5,776,183 A | | 7/1998 | Kanesaka et al. |
| 5,895,406 A | * | 4/1999 | Gray et al. ................... 623/1.15 |
| 5,928,280 A | | 7/1999 | Hansen et al. |
| 6,019,789 A | | 2/2000 | Dinh et al. |
| 6,027,526 A | * | 2/2000 | Limon et al. ................. 623/1.15 |
| 6,027,527 A | | 2/2000 | Asano et al. |
| 6,042,606 A | | 3/2000 | Frantzen |
| 6,096,070 A | * | 8/2000 | Ragheb et al. ............... 623/1.39 |
| 6,106,548 A | | 8/2000 | Roubin et al. |
| 6,193,744 B1 | | 2/2001 | Ehr et al. |
| 6,206,911 B1 | | 3/2001 | Milo |
| 6,261,319 B1 | | 7/2001 | Kveen et al. |
| 6,264,685 B1 | | 7/2001 | Ahari |
| 6,368,355 B1 | | 4/2002 | Uflacker |
| 6,451,052 B1 | | 9/2002 | Burmeister et al. |
| 6,485,524 B2 | | 11/2002 | Strecker |
| 6,488,702 B1 | | 12/2002 | Besselink |
| 6,540,777 B2 | | 4/2003 | Stenzel |
| 6,669,718 B2 | | 12/2003 | Besselink |
| 6,755,856 B2 | | 6/2004 | Fierens et al. |
| 6,772,836 B2 | | 8/2004 | Schetky et al. |
| 6,799,637 B2 | | 10/2004 | Schetky et al. |
| 7,235,097 B2 | | 6/2007 | Calisse et al. |
| 7,291,166 B2 | | 11/2007 | Cheng et al. |
| 7,300,458 B2 | | 11/2007 | Henkes et al. |
| 7,476,245 B2 | | 1/2009 | Abbate |
| 2001/0027339 A1 | * | 10/2001 | Boatman et al. ............. 623/1.15 |
| 2002/0035394 A1 | | 3/2002 | Fierens et al. |
| 2003/0074052 A1 | | 4/2003 | Besselink et al. |
| 2003/0199969 A1 | | 10/2003 | Steinke et al. |
| 2004/0088043 A1 | | 5/2004 | Klein |
| 2004/0133270 A1 | | 7/2004 | Grandt |
| 2004/0193247 A1 | | 9/2004 | Besselink et al. |
| 2005/0163821 A1 | | 7/2005 | Sung et al. |
| 2006/0217795 A1 | | 9/2006 | Besselink et al. |
| 2008/0097571 A1 | | 4/2008 | Denison et al. |
| 2009/0187243 A1 | * | 7/2009 | Johnson ..................... 623/11.11 |

FOREIGN PATENT DOCUMENTS

| | | |
|---|---|---|
| EP | 0 326 426 A2 | 8/1989 |
| EP | 0 335 341 A1 | 10/1989 |
| EP | 0 364 787 A1 | 4/1990 |
| EP | 0 421 729 A2 | 4/1991 |
| EP | 0 540 290 A2 | 5/1993 |
| EP | 0587 197 A1 | 3/1994 |
| EP | 0 636 345 A1 | 2/1995 |
| EP | 0 664 107 A1 | 7/1995 |
| EP | 0 679 372 A2 | 11/1995 |
| EP | 0 688 545 A1 | 12/1995 |
| EP | 0 734 698 A2 | 10/1996 |
| EP | 0 744 164 A1 | 11/1996 |
| FR | 2 617 721 A1 | 1/1989 |
| FR | 2 642 812 A1 | 8/1990 |
| GB | 2 081 173 A | 2/1982 |
| GB | 2 169 515 A | 7/1986 |
| GB | 2 175 824 A | 12/1986 |
| WO | WO 92/06734 A1 | 4/1992 |
| WO | WO 92/19310 A1 | 11/1992 |
| WO | WO 93/22986 A1 | 11/1993 |
| WO | WO 94/03127 A1 | 2/1994 |
| WO | WO 95/09584 A1 | 4/1995 |
| WO | WO 95/31945 A1 | 11/1995 |
| WO | WO 95/32757 A1 | 12/1995 |
| WO | WO 96/03942 A2 | 2/1996 |
| WO | WO 96/09013 A1 | 3/1996 |
| WO | WO 96/18359 A2 | 6/1996 |
| WO | WO 96/29028 A1 | 9/1996 |
| WO | WO 96/41589 A1 | 12/1996 |
| WO | WO 97/04721 A1 | 2/1997 |

OTHER PUBLICATIONS

U.S. Appl. No. 10/782,266 and its prosecution history including the Office Action mailed Oct. 18, 2007, and the Amendments filed May 6, 2008 and Mar. 18, 2008.

U.S. Appl. No. 10/782,266 and its prosecution history including the Office Action mailed Jul. 18, 2008, Oct. 18, 2007, and the Amendments filed Oct. 20, 2008, May 6, 2008 and Mar. 18, 2008.

U.S. Appl. No. 10/782,266, filed Feb. 18, 2004, published US 2004-0193247, and its ongoing prosecution history, including without limitation an Amendment filed May 26, 2009, a Final Office Action mailed Jan. 26, 2009, an Office Action mailed Jul. 18, 2008, a Final Office Action mailed Sep. 29, 2009, an Amendment filed Nov. 23, 2009, and a Supplemental Amendment filed Jan. 25, 2010.

U.S. Appl. No. 11/391,940, filed Mar. 29, 2006, published as US 2006-0217795 on Sep. 28, 2006 and its ongoing prosecution history, including but not limited an Amendment filed Oct. 22, 2009, and an Office Action mailed Dec. 9, 2009.

U.S. Appl. No. 10/270,771, filed Oct. 11, 2002, published as US 2003-0074052, and its ongoing prosecution history, including without limitation an Amendment filed Jun. 18, 2009; a Notice of Allowance mailed Aug. 11, 2009, and an Office Action mailed Jan. 27, 2010.

U.S. Appl. No. 11/391,940, filed Mar. 29, 2006, published as US 2006-0217795 on Sep. 28, 2006, and its ongoing prosecution history, including without limitation a Final Office Action mailed Apr. 23, 2009, an Amendment filed Jan. 22, 2009, and a Non-Final Office Action mailed Aug. 22, 2008.

U.S. Appl. No. 10/782,266, filed Feb. 18, 2004, publidhed as US 2004-0193247, and its ongoing prosection history, including without limitation an Amendment filed May 26, 2009, and a Non-Final Office Action mailed Jan. 26, 2008.

U.S. Appl. No. 10/270,771, filed Oct. 11, 2002, published as US 2003-0074052 on Apr. 17, 2003, and its ongoing prosecution history, including without limitation a Notice of Allowance mailed Aug. 11, 2009; an Amendment filed Jun. 18, 2009; an Amendment filed Sep. 22, 2003, and a Non-Final Office Action mailed Jul. 29, 2003.

U.S. Appl. No. 11/875,718, filed Oct. 19, 2007, published as US 2008-0097571 on Apr. 24, 2008, and its ongoing prosecution history.

* cited by examiner

DEVICE COMPRISING BIODEGRADABLE BISTABLE OR MULTISTABLE CELLS AND METHODS OF USE

REFERENCE TO RELATED APPLICATIONS

The present application is a continuation-in-part of U.S. patent application Ser. No. 10/270,771, filed Oct. 11, 2002, which is a continuation of U.S. patent application Ser. No. 09/012,843, filed Jan. 23, 1998, now U.S. Pat. No. 6,488,702, which claims the benefit of priority of U.S. provisional application Ser. No. 60/036,359, filed Jan. 24, 1997.

FIELD OF THE INVENTION

The present invention relates to devices for medical and non-medical applications comprising biodegradable bistable or multistable cell structures capable of transitioning between contracted and expanded states.

BACKGROUND OF THE INVENTION

Commercially available previously-known stents typically are either balloon expandable or self expanding. Both types of stents suffer from a host of drawbacks, including recoil, foreshortening and, in the case of self-expanding stents, imprecision in deployment location.

Balloon expandable stents are generally made from a material that is readily plastically deformed into two directions. Before insertion, the stent is placed around the balloon section at the distal end of a catheter and crimped onto the balloon. Once the stent is positioned at a target location within the body, it is deployed by inflating the balloon to plastically deform the stent. The stent is at its largest diameter and should function to support the surrounding tissue when deployed, and to prevent an undesired reversion to a smaller diameter.

Therefore, stents generally require sufficient rigidity in the radial direction to retain the vessel patent, but also some flexibility in the axial direction when deployed so as to not reform the vessel. Further, the stent preferably should use as small an amount of material as possible and its interior surface should not obstruct the flow through the channel (e.g., for blood) or cause too much turbulence.

A number of problems are generally known to occur with balloon expandable stents. For example, after the stent is compressed to its smallest diameter around the balloon of the delivery catheter, the stent is subject to some elastic return to a slightly larger diameter. This may cause problems when the catheter is brought into the patient's body, for example, if friction between balloon and stent becomes so small that the stent slips off the catheter. Further, the larger size of the stent disadvantageously presents a larger delivery profile.

A further problem with previously-known commercially available balloon expandable stents is so-called "recoil." Recoil refers to the fact that, after expansion by the balloon pressure, the outer diameter of the stent becomes slightly smaller when the balloon is deflated. This effect may result in the stent having as much as a 10% decrease in deployed diameter, which can lead to undesirable migration of the stent. In addition, in an effort to offset recoil, a clinician may overexpand the stent during balloon inflation, which may lead to excessive trauma to the vessel endothelium and exacerbate restenosis.

Self-expanding stents are made of a more or less elastically expanding structure, which has to be held on the catheter by some external means. An example of this type is a stent that is held in its constrained state by a delivery sheath. The stent deploys to its expanded shape when the sheath is removed. Self-expanding stents also may be constructed of a shape memory material that exhibits either superelastic behavior or which is expanded by a temperature change. Self-expanding stents suffer from a number of drawbacks, including increased delivery profile resulting from use of a delivery sheath and inaccurate placement resulting from stent movement during deployment.

The foregoing previously-known types of stents further have the disadvantage of relatively large length change during expansion and a poor hydrodynamic behavior because of the shape of the metal wires or struts.

Another disadvantage of some stents is the positive spring rate, which means that further expansion can only be achieved by higher balloon pressure.

The construction of prior stents is typically made in such a way that the external forces, working on the stent in the radial direction, merely cause bending forces on the struts or wires of the structure.

For example, a unit cell of a Palmaz-Schatz-stent, as produced by Cordis Corporation has in its collapsed condition a flat, rectangular shape and in its expanded condition a more or less diamond-shaped form with almost straight struts or curved struts.

The shape of the unit cell of such stents is typically symmetrical with four struts each having the same cross section. In addition, the loading of the cell in the axial direction typically will cause an elastic or plastic deformation of all of the struts, resulting in an elongation of the unit cell in the radial direction. These unit cells have a positive spring rate. In stents having such unit cells, the stability against radial pressure is dependent primarily on the banding strength of the struts and their connections.

To address some of the concerns encountered with previously-known stents, especially restenosis, it has been suggested to make stents out of a biodegradable material. One example of such a stent is described in U.S. Pat. No. 5,449,382 to Dayton, which describes rolled-sheet stents made, for example, of biodegradable polylactic acid polymers or polyglycolic acid polymers. The stents are impregnated with a drug that is released into the vessel during biodegradation of the stent to reduce thrombosis or restenosis.

U.S. Pat. No. 6,488,702 to Besselink, of which the present application is a continuation-in-part, discloses a new type of unit cell that may be incorporated into a stent to address the shortcomings of previously-known stents. That patent discloses a tubular device, such as a stent, comprising a plurality of bistable or multistable unit cells. Those unit cells are described as having only a discrete number of stable configurations, and snap from one stable configuration to the next upon application of a suitably directed radial force. The devices described in that patent advantageously overcome many of the problems encountered with previously-known plastically deformable and self-expanding stents.

The aforementioned Besselink patent describes that devices having bistable and multistable unit cell structures may be constructed of metal alloys, polymers and shape memory materials, such as nickel-titanium alloys. When configured as stents, such structures will endothelialize once deployed within a body vessel. However, situations may arise where it would be desirable to capture the benefits afforded by using a bistable or multistable unit cell in conjunction with a drug eluting capability.

It would therefore be desirable to provide a stent comprised of bistable or multistable unit cells, and which is formed from a biodegradable material.

It further would be desirable to provide a stent comprised of bistable or multistable unit cells, and which provides in addition a drug delivery capability.

SUMMARY OF THE INVENTION

In view of the foregoing, it is an object of this invention to provide an expandable device comprised of bistable or multistable unit cells, and which is formed from a biodegradable material.

It is a further object of this invention to provide a device comprised of bistable or multistable unit cells, and which provides in addition a drug delivery capability.

These and other objects of the present invention are accomplished by providing an expandable support device comprising a unit cell formed of a biodegradable material and having a negative spring rate and a bistable or multistable function. As defined herein, a multistable function is one in which the device is capable of assuming only a discrete number of stable configurations, A "bistable" device, for example, is stable only in its stable fully contracted configuration and stable fully expanded configuration, and will transition to one of these two stable configurations when released from external restraint. For the purposes of this application, the term "multistable" is intended to include "bistable".

The device constructed in accordance with the present invention may be used in a wide variety of medical and non-medical applications, but is expected to be especially useful in the construction of biodegradable and/or drug eluting stents. In preferred embodiments, the device of the present invention is molded, cast, deposited using stereolithography, or machined from the group of materials consisting of poly(L-lactide-co-glycolide), polyhydroxyalkanoate, polyester amide, a chitosan and genipin structure or a silicon and iron composite material.

In another embodiment, the device is machined from a piece of tubing. The tubing may be formed in a variety of ways, including dip molding, extrusion, and sheet rolling. In a dip molding method, a biocompatible material is dissolved in an appropriate solvent to form a solution of having desired consistency. A mandrel then is repeatedly dipped and withdrawn from the solution, allowing adequate time between dippings for the solvent to at least partially dry. The process is repeated a number of times to attain a desired tubing wall thickness. The resulting tube then may be machined using a laser source such as an excimer laser, femto-second laser, or NdYAG laser. Alternatively, mechanical machining techniques may be employed, including the use of water-jets and other focused-energy machining techniques. As a yet further alternative, components and/or sections of the device may be fabricated individually and subsequently joined or otherwise placed in communication with each other, for example, by welds or adhesive connections.

In accordance with the principles of the present invention, a stent embodiment of the expandable device comprises a biodegradable material that forms unit cells having two or more stable configurations, i.e., in which the stent is stable without the need for an external force to hold it in that shape. Preferably, the unit cell is formed using at least two different sections, wherein a less pliable section acts as a relatively rigid support that hinders shape change of a more pliable section in one direction. The pliable section may be deformed in the other direction, but due to the opposing force supplied by the rigid section, the stability of the pliable or flexible section is greatly increased.

External forces in a direction perpendicular to the most pliable section are distributed to the rigid section and the cross section of the pliable section is merely loaded in a compression mode. This makes the construction much stronger than previously-known expandable support devices.

The device of the present invention may be readily elastically compressed around the balloon of a deployment system, such as a balloon catheter. Below a certain critical diameter, the device snaps further to a stable, smallest diameter, thus holding the deflated balloon firmly on to the surface of the delivery system, After the device is disposed at a target deployment site, the delivery system is actuated to apply a radially outward force until the device reaches its critical elastic equilibrium diameter. Slightly above this diameter the device will automatically expand to its largest diameter, at which it attains its maximum stability against radial pressure. The design enables a constant length large expansion ratio, a reliable expandability and/or a small surface ratio.

By varying the relative rigidities of the rigid and pliable sections of the unit cells, a plurality of different unit cells may be constructed within a single device, thus providing the possibility of stepwise expanding of the device with a range of stable expanded diameters. The device of the present invention also may employ unit cells that provide several different external diameters along the length of the device, thereby enabling the device to conform to the shape of the cavity in which it is deployed. Still further, the unit cells may be constructed so that the force displacement characteristic of the unit cell becomes asymmetrical, with either the expanded diameter or the collapsed diameter being the most stable configuration.

BRIEF DESCRIPTION OF THE DRAWINGS

The above and other objects and advantages of the present invention will be apparent upon consideration of the following detailed description, taken in conjunction with the accompanying drawings, in which like reference characters refer to like parts throughout, and in which.

DETAILED DESCRIPTION OF THE INVENTION

Figure 1A:
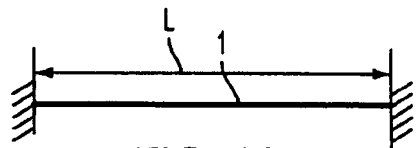
FIG. 1 shows the principle of a bistable mechanism.

The expandable support device of the present invention comprises a plurality of unit cells formed of a biodegradable material and which are stable only in two or more discrete configurations. Although the present invention is illustratively described for use as a stent for medical applications, it should be understood that a device constructed in accordance with the principles of the present invention may be advantageously used in other medical and non-medical applications.

Each unit cell comprises at least two distinct, mechanically connected sections having different mechanical behaviors. One section acts as a relatively rigid support for the more flexible counteracting section. The more flexible section is responsible for most, if not all, of the expansion of the device. In accordance with one aspect of the present invention, the unit cells of the device are molded, cast, deposited using stereolithography, or machined from a biodegradable material. Preferred materials include poly(L-lactide-co-glycolide), such as Resomer LG 824 manufactured by Boehringer Ingelheim, Ingelheim, Germany, polyhydroxyalkanoate, marketed under the TephaFlex name by Tepha, Inc., Cambridge, Mass., PEA 4-Phe(DAS)Phe(4) (a type of polyester amide) manufactured by MediVas, Inc., San Diego, Calif., a chitosan and genipin structure offered by Genistent Medical Corp., Irvine, Calif. and a biodegradable silicon and iron composite material, offered by pSiMedica Ltd., Perth, Western Australia.

It is further contemplated that the present invention may be fabricated from a combination of two or more materials. For example, an inner bi-stable structure may be fabricated from one of the materials described above or of other biocompatible materials such as nitnol, stainless steel, cobalt chromium, or multi-layer materials such as those shown and described in U.S. Pat. No. 5,858,556 to Eckert et al., the entirety of which is hereby incorporated by reference. A second material, preferably a bio-absorbable material such as those described above, then may be disposed about the inner core, thereby forming a composite bi-stable stent. Such a composite bi-stable stent advantageously may optimize the mechanical properties unique to each material, thereby enhancing performance of the device.

A further method of making the device of the present invention comprises creating a pattern of slits or slots in the wall of a tubular member by etching, grinding, cutting (e.g., with a laser, water-jet, etc.), spark erosion or any other suitable method. As further alternative, the unit cells may be formed as a flat plate and then glued, welded or crimped to a more or less tubular shape.

The tubing may be formed in a variety of ways, including dip molding, extrusion, and sheet rolling. In a dip molding method, a biocompatible material is dissolved in an appropriate solvent to form a solution of having desired consistency. A mandrel then is repeatedly dipped and withdrawn from the solution, allowing adequate time between dippings for the solvent to at least partially dry. The process is repeated a number of times to attain a desired tubing wall thickness. The resulting tube then may be machined using laser or mechanical machining techniques, such as water-jets and other focused-energy machining techniques. As a yet further alternative, components and/or sections of the device may be fabricated individually and subsequently joined or otherwise placed in communication with each other, for example, by welds or adhesive connections.

It is contemplated that conventional stent fabrication techniques, such as laser-cutting a stent from a single tube using an excimer laser, may not be suitable for the bioabsorbable materials intended to be used to make the devices of the present invention. Accordingly, to reduce the risk of oxidation and melting and to reduce and/or eliminate the heat affected zone, it may be necessary to use a femto-second laser or a NdYAG laser to fabricate the inventive devices.

Further in accordance with the present invention, the biodegradable material may be impregnated with a anti-stenotic drug or other drug or bioactive agent so that the drug or bioactive agent is delivered into the patient's bloodstream or vessel wall during biodegradation of the device.

Figure 1B:
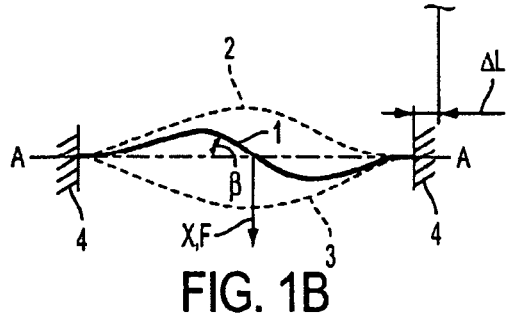
Figure 1C:
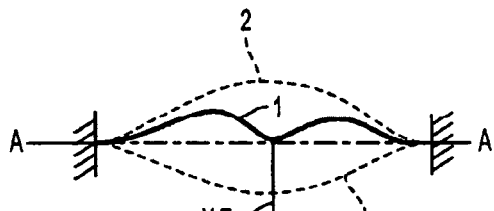

Referring to FIGS. 1a-1c, the principle upon which the device of the present invention is described. FIG. 1a shows rod 1 with length L, which is compressed in its axial direction. When the rod reaches its buckling stress, as shown in FIG. 1b, the central part of the rod will bow out in a sidewards direction, either to position 2 or 3 (depicted by dashed lines in FIG. 1b). When the axial displacement L of the ends of the rod is held stable by external clamps 4, it is possible to move the central section of the rod between the two stable positions 2 and 3. This movement is in a direction X, perpendicular to the original length axis A-A of the rod. All positions between the stable positions 2 and 3 are unstable. As depicted in FIG. 1b, the central part of the rod has to rotate over an angle β before the rod can be moved in direction X. FIG. 1C shows a second order curvature in rod 1, which occurs when the rotation over angle β is opposed by clamping the central part of rod 1 and maintaining this part parallel to the axis A-A.

Figure 2:
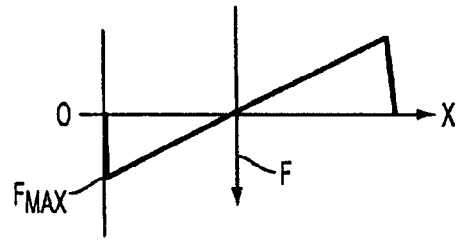
FIG. 2 shows the force-displacement characteristic of the mechanism of FIG. 1.

FIG. 2 shows the force F as a function of displacement X, with X displayed in the horizontal direction. The rod is moved from the upper stable position 2 to the lower stable position 3 of FIG. 1. The force increases rapidly from zero to $F_{max}$. At that moment the onset of either the first or second order curvature of FIGS. 1b and 1c is reached. Further displacement in direction X requires less force, because this spring system has a negative spring rate. The force even becomes zero in the mid position and further movement occurs automatically. It can be seen in FIG. 2 that the system is completely symmetrical and the force needed to move back from the lower to the upper position has the same characteristic.

Figure 3:
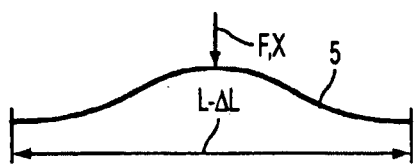
FIG. 3 shows a bistable mechanism having asymmetric bistability.

FIG. 3 shows rod 5 that has an asymmetrical force displacement characteristic. This is so because rod 5 already has a preset curvature, even in the unloaded position, where the length is already L-L. This may be achieved by prior plastic deformation, heat treatment or the use of an asymmetrical geometry of the cross section of the rod (not shown). Rod 5 in FIG. 3 can be mounted between two clamps on a length L-L, and if it is elastically deformed in the same way as the rod in FIGS. 1b and 1c, it will have a different stress distribution in the cross section in end positions 2 and 3, compared to the rod of FIG. 1. This means that the rod has a preferred unloaded/stable position, shown in FIG. 3.

Figure 4:
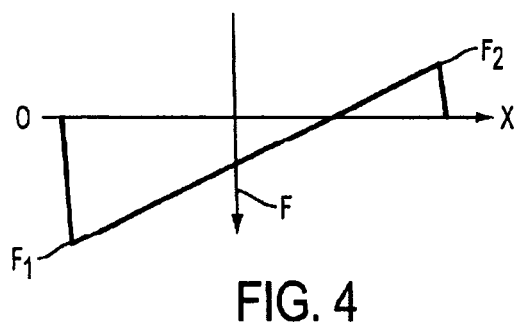
FIG. 4 shows the force-displacement characteristic of the mechanism of FIG. 3.

With respect to FIG. 4, the asymmetrical force-displacement characteristic of the precurved rod of FIG. 3 is described. The initial displacement form the stable upper position needs a starting force $F_1$ and if the rod is in its stable lower position, the starting force in the opposite direction is only $F_2$, being smaller than $F_1$. Force $F_2$ can be made as small as desired, even zero or negative, but needs to have a positive value if stability of the lower position is required.

Figure 5A:
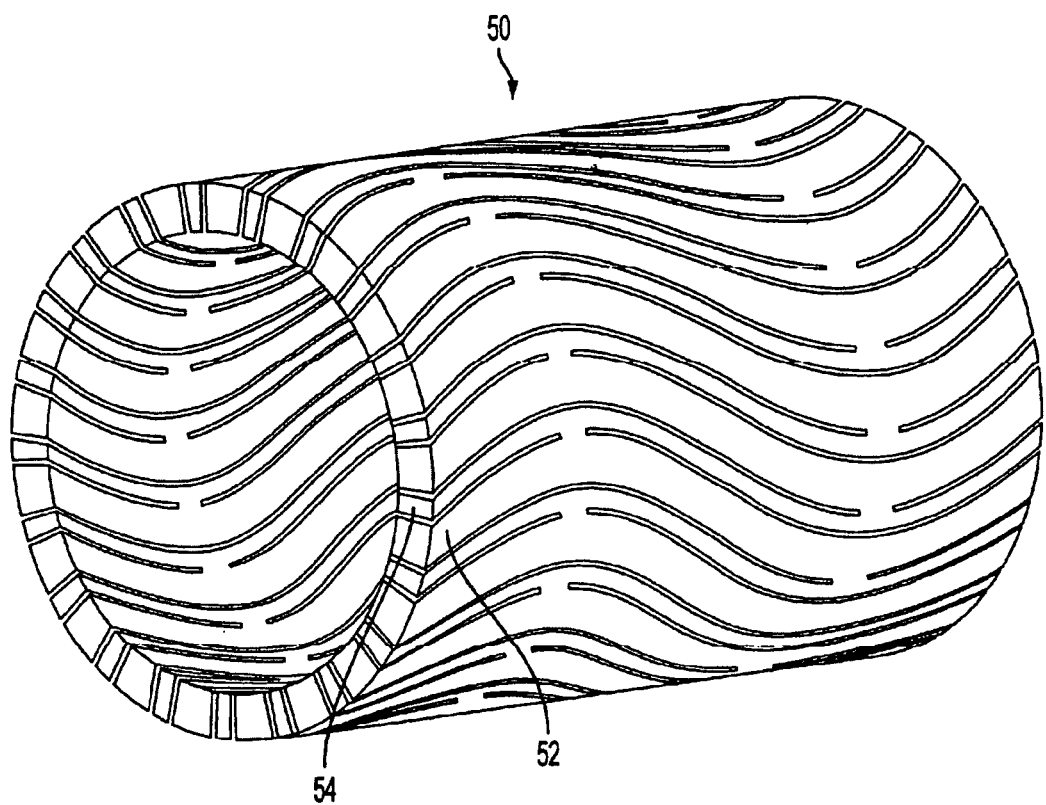
FIGS. 5a and 5b show, respectively, an expandable tubular device of the present invention in the stable, fully collapsed configuration and the stable fully expanded configuration.
Figure 5B:
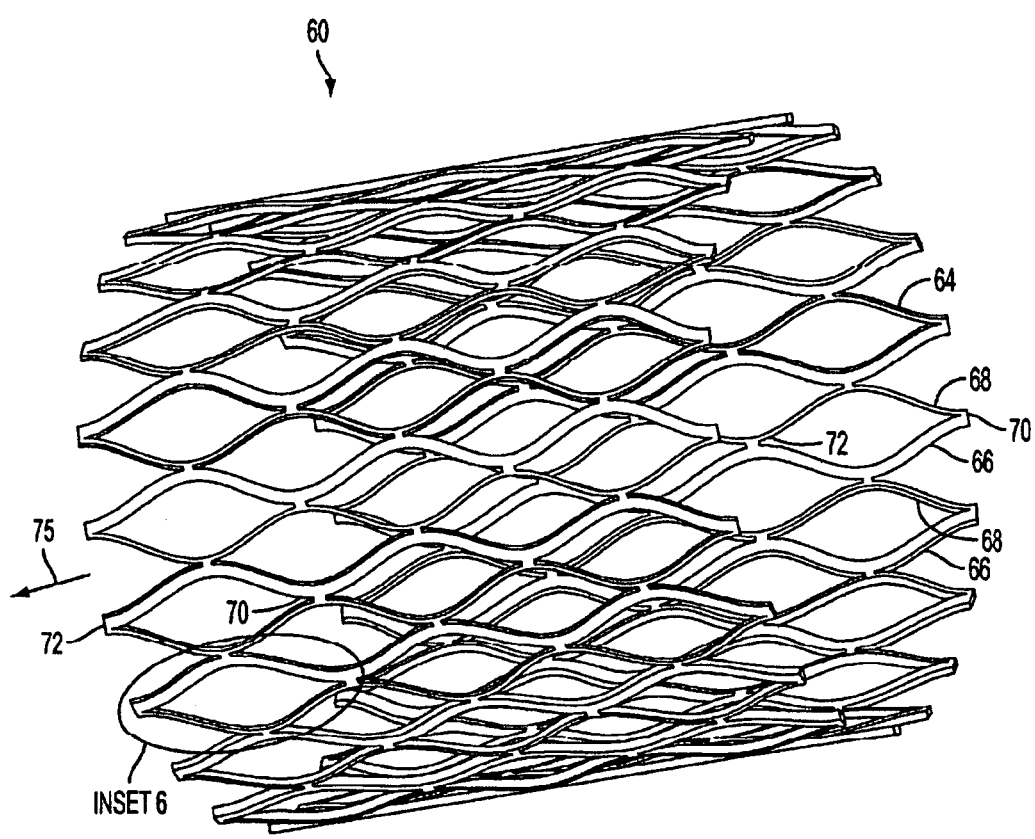

FIGS. 5a and 5b show the general appearance of an inventive tubular stent in a fully contracted configuration and fully expanded configuration, respectively. The stent, in its fully contracted state shown generally at 50 and in its fully expanded state shown generally at 60, is comprised of a plurality of interconnected bistable unit cells (shown in the expanded state at 64 in FIG. 5b). The bistable unit cells are formed from a first relatively rigid segment 52 (66 in FIG. 5b) and a second relatively flexible segment 54 (68 in FIG. 5b), joined together at ends 70 and 72. Second relatively flexible segments 68 are interconnected with adjacent relatively rigid members 66. Adjacent cells in the longitudinal sense (the longitudinal axis is denoted by reference numeral 75) are joined at ends 70 and 72. By applying a uniform radially outward or inward force, the stent may be switched directly from a fully contracted to a fully expanded configuration or vice versa.

Figure 6:
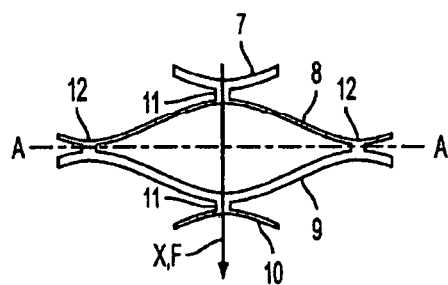
FIG. 6 shows a part of a device with one bistable unit cell, drawn in the stable expanded shape.

FIG. 6 (corresponding to inset 6 in FIG. 5b) shows a small part of a stent such as that shown in FIG. 5 which uses the bistable function of a unit cell, according to the present invention. The drawing shows a horizontal line A-A, which is parallel to the central axis of the stent. There are two series of sinusoidal segments with distinct size (see also FIG. 9 for an overview). The segments 7 and 9 have a relatively large cross section. Only segment 9 is shown entirely. The segments 9 and 10 have a relatively smaller cross section, and here only segment 8 is entirely shown. The segments are interconnected for example welded, at joints 11 and 12.

Because of the difference between the cross section of segment 8 and 9, the deformation force of segment 8 is much lower than for segment 9. Therefore, segment 9 can be considered as a relatively rigid clamp, like the clamps 4 in FIG. 1b opposing relative displacement between the joints 12 in the axial direction, parallel to axis A-A. In contrast, segment 8 acts as a flexible rod, like rod 1, described in FIG. 1 or rod 5, described in FIG. 3. This combination of segments 7 and 8 or 9 and 10 defines a unit cell, acting as a bistable spring system with a force-displacement curve F-X like the described curves of FIGS. 2 and 4, depending on the unloaded condition and geometry of the segments.

Alternatively, instead of using segments or struts of different diameter, the segments can have the same diameters (i.e., cross sectional area) and exhibit different strengths or rigidity and still accomplish the same effect. One way to obtain such differences in strength or rigidity would be to use different materials for the segments. Another way would be to use the same material, like a metal, for all the segments but selectively strengthen (e.g., by heat treating) those segments that need to be rigid. It should be noted that heat treatment will not strengthen all materials. Nitinol, for example becomes more pliable as a result of heat treatment. This property of Nitinol can be exploited, however, to render one section of Nitinol more pliable relative to a second, non-heat-treated section of Nitinol.

Figure 7:
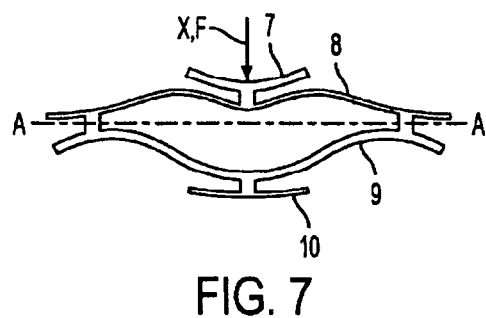
FIG. 7 shows the part of the device of FIG. 6 near its elastic bistable equilibrium position.

FIG. 7 shows the same part of the stent (as depicted in FIG. 6) near the elastic equilibrium position at which the flexible segment transitions from the first to the second stable configuration. Segment 8 has been deformed in the direction X by force F, but segment 9 has almost its original shape because it is more rigid.

Figure 8:
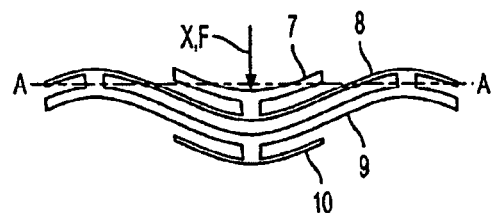
FIG. 8 shows the part of the device of FIGS. 6 and 7 in its stable collapsed shape.

FIG. 8 shows the same unit cell of the stent of FIGS. 6-7 after it has been pressed through the elastic equilibrium position. It automatically snaps into its stable position of FIG. 8. This snapping force can be strong enough to hold a deflated balloon tight on the catheter shaft (not shown), depending on the mechanical characteristics (e.g., the strength) of the material(s) used to make the segments. With the geometry shown in these figures, the segments 8 and 9 fit close together, taking up a minimum amount of space when the stent is in its smallest stable diameter.

Figure 9:
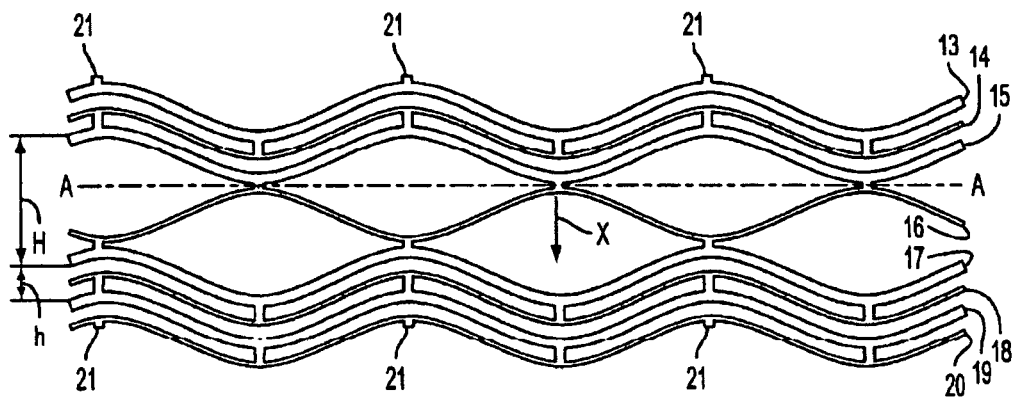
FIG. 9 shows a larger section of the device of FIGS. 6 and 8, showing some unit cells in the collapsed shape and some unit cells in the expanded shape.

FIG. 9 shows a section of the stent of FIG. 5, flattened for illustrative purposes, showing several flexible segments in the collapsed stable shape (segments 14, 18 and 20) and one segment element 16 in the expanded stable shape. Segments 13, 15, 17, and 19 are relatively rigid segments and substantially maintain their original shape. The distance between two relatively rigid segments is shown as (h) in the collapsed stable shape and (H) in the expanded stable shape. The value of the displacement (H−h) in the direction X depends on the height of an expanded unit cell or amplitude of the segments and the size of the connecting joints. The described part of the stent is shown as a flat surface, but it may be clear that a cylindrical stent such as that shown in FIG. 5 is shaped if segments 13 and 20 are directly connected to each other with joints 21. In other words, the stent is shown separated along the joints 21 and in a flattened condition.

The range of stable diameters of the stent changes with the value (H−h)/n, each time that a flexible segment snaps from the collapsed stable position to the expanded stable position. The result is a stent with an extremely rigid surface at all diameters, which is able to withstand external forces better than conventional stents. In the length direction, the flexibility of the stent may be increased by disconnecting several unit cells from their neighboring unit cells, for example, by cutting the center of one or more joints while maintaining the several joint pieces as joints.

Another method to increase flexibility is to change the geometry of several sections of the unit cells in the length direction from the relatively flexible to the relatively rigid shape several times along the total length of the stent. In other words, referring to FIG. 9 one or more or each of the segments 13-20 could be constructed with larger and smaller diameter (or otherwise flexible and rigid) sections which alternate after each joint 21.

Figure 10:
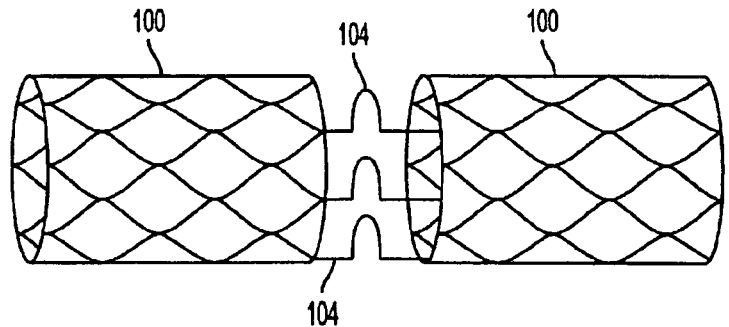
FIG. 10 shows an inventive device formed of a plurality of smaller inventive tubes joined together with flexible connectors.

Another possibility, as shown in FIG. 10 is the use of a series of short multistable stents 100 aligned lengthwise end to end and connected with flexible joints 104 having the same or a different geometry or configuration as the joints forming individual unit cells.

In a more general sense, the present invention is directed to a tubular device having a plurality of stable configurations. The device is comprised of a plurality of interconnected multistable cells. The cells include one or more relatively rigid sections and one or more relatively flexible sections interconnected so as to define a cell structure in the form of a multistable spring system having a plurality of stable configurations. In a preferred embodiment, the cells comprise a first arcuate member having first and second ends and a second arcuate member having first and second ends, the first end of the first member in communication with the first end of the second member, and the second end of the first member in communication with the second end of the second member. It should be noted, however that members need not be rigorously arcuate. Other shaped members, including relatively straight members are contemplated as well.

The invention, in particular, contemplates devices comprising bistable cells, that is cells having two stable configurations. In one such cell, the distance between corresponding points on the first and second sections is larger in the first stable state of the cell than in the second stable state of the cell. The cells themselves are constructed and arranged so that the device itself is at least bistable and possibly multistable. One such device, illustratively a cylindrical stent having two or more configurations with an initial diameter size and a final larger diameter size, has been described above.

However, multistable devices also are contemplated. Thus, for example, a device may be constructed in which the cells are designed and arranged to provide a range of diameters in step-wise fashion. One such way this may be accomplished would be to employ several different types of cells in the device, each type of cell having a different spring constant so that depending on the amount of force used, the device would assume a different diameter. Such a device in a partially expanded state is shown schematically in FIG. 11. A partially expanded device is shown generally at 120. The device comprises relatively rigid segments 123, 127, 131 and 135 which substantially maintain their original shape, and relatively flexible segments 125, 129, and 133. It should be understood that in keeping with the stated functionality of the embodiment of FIG. 11, while rigid segments 123, 127, 131 and 135 may be of uniform thickness, flexible segments 125, 129 and 133 have different thicknesses, thus providing the desired step-wise expansion characteristic.

Figure 11:
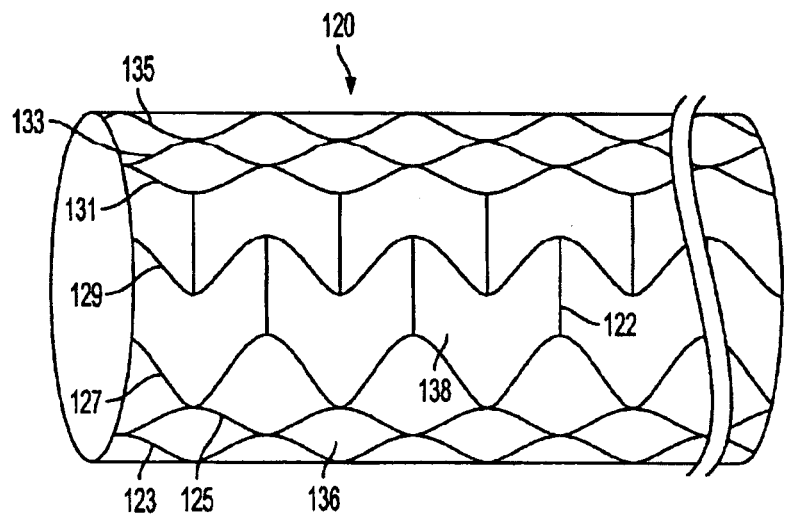
FIG. 11 shows a partially expanded inventive device having more than one type of bistable unit cell.

The foregoing segments are interconnected by joints 122. As depicted, first flexible elements 125, and 133 are in an expanded configuration while second flexible element 129 is in a contracted configuration. By applying a radially outward or tangential force, flexible element 129 may be flipped to its fully expanded configuration resulting in a device (not shown) with a larger diameter. As shown in FIG. 11, cells 138 are larger than cells 136 even in the contracted state. First flexible elements 125 and 133 are characterized by a different degree of flexibility than second flexible element 129.

Figure 12:
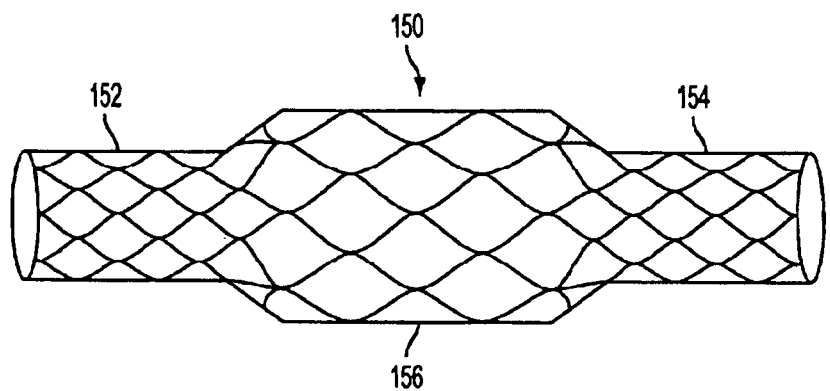
FIG. 12 shows an inventive device having a range of diameters along its length.

Another form of device, suitable for use as a stent shown generally at 150 in FIG. 12, has a first diameter at first end 152, a second diameter at second end 154 and one (or more) intermediate diameters in region 156 between first end 152 and second end 154. As shown in FIG. 12, the intermediate diameter differs from the first and second diameters. The interconnected cells in such a device, as shown generally at 150 in FIG. 12, may all have the same force constant and hence may be opened all at once with the application of the necessary force. Alternatively, several different types of cells may be used, each with its own force constant. In order to achieve a multiplicity of diameters, cells of differing sizes may be used. In one embodiment, the first and second diameters are the same while in another embodiment, the first and second diameters differ.

The present invention also is directed to a method of implanting an expandable device having a plurality of stable configurations within a passageway, such as in stenting a blood vessel. The method comprises steps of applying the stent to an expanding means on a catheter, such as a balloon; delivering the stent to a desired bodily location; expanding the expanding means so as to expand the stent from a first stable configuration to a desired second stable configuration, the second stable configuration having a larger diameter than the first stable configuration, and deploying the expanded stent at the desired bodily location.

The expanding means may be a balloon, a mechanical device on or in the catheter, a heat source where the cells can be induced to change states by heating or any other suitable expanding means. The stent may be applied to the balloon in the first stable configuration or may be applied in the second stable (expanded) configuration during the applying step. In the latter case, radially inward pressure may be applied to the stent so as to urge the stent into the first stable configuration to snap it onto the catheter. Where the stent has additional stable states, the stent may be applied to the balloon in an intermediate stable state in which the diameter of the stent is intermediate between the diameter in the first state and the diameter in the second state. Again, the stent may be locked on the expanding means by further applying a radially inward pressure.

The unit cell of the present invention also is directed to an expandable tubular device having unexpanded and expanded configurations, the device comprising a plurality of generally longitudinal, wave-like first members characterized by a first wavelength, and having peaks and troughs, and a plurality of generally longitudinal wave-like second members characterized by a second wavelength, and having peaks and troughs. The wavelengths of the first and second longitudinal members are substantially equal.

The second members are capable of stably assuming two positions, a first position corresponding to the unexpanded configuration in which the first and second members are in phase and a second position corresponding to the expanded configuration, in which the first and second members are 180° out of phase. The first members are more rigid than the second members. The first and second longitudinal members are disposed on the surface of the stent such that the longitudinal first and second members alternate.

In the unexpanded state, each peak of each first member is connected to one adjacent peak of a second member in a region of attachment and each trough of each first member is attached to one adjacent trough of a second member in a region of attachment, as can be seen from FIG. 8. The regions of attachment are separated along the longitudinal direction by one wavelength. The above-described device can be snapped from the unexpanded configuration to the expanded configuration by applying a radially outward force. Similarly, the device can be snapped from the expanded to the unexpanded configuration by applying a radially inward force. While such devices may be used internal to a bodily vessel, it may also be used external to vessels to join two vessels together.

Referring now to FIGS. 13a and 13b, multistable unit cells of the present invention having other shapes are described. The contracted cell, shown generally at 700, and the expanded cell, shown generally at 705, consist of four interconnected relatively rigid members. Two side members 709 are connected to opposite ends of top member 713 via hinges 715. Side members 709 are connected at their opposite ends to opposite ends of bottom member 717 via hinges 719. Preferably, the hinges are elastic or plastically deformable. The hinges may be fixedly attached to the side, top and bottom members or may be integral with these members. In the latter case, the hinges may be formed by removing material from the cell in the region of the hinges so that the hinges are thinner or have a different geometry from the side, top and bottom members. In the process of transitioning from the expanded to the collapsed state, bottom member 717 opens slightly. The cell of FIGS. 13a and 13b also have two additional intermediate states in which one or the other (but not both) of side members 709 and top member 713 are collapsed downward.

Figure 14:
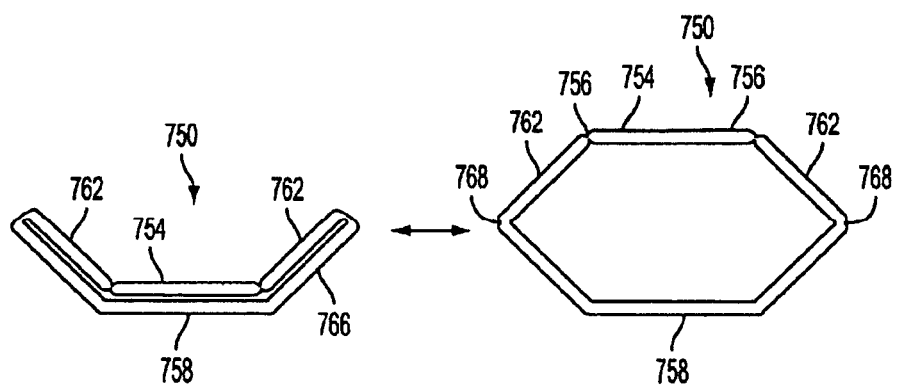
FIGS. 14a and 14b show, respectively, an alternative multistable cell in the fully contracted state and in the fully expanded state.

Referring to FIGS. 14a and 14b, a hexagonal hinged multistable unit cell is described. The unit cell is depicted in FIG. 14a in the collapsed state and in FIG. 14b in the expanded state. The cell, shown generally at 750, consists of top member 754 and bottom member 758, and upper side members 762. Two upper side members 762 are connected to opposite ends of top member 754 via hinges 756. Upper side members 762 are connected to bottom member 758 via hinges 768. Bottom member 758 is shaped like a "U" with the two uprights of the "U" modified to lie at oblique angles with respect to the bottom part of the "U".

As with the previously discussed inventive cells, hinges 756 and 768 may be elastic or plastically deformable and may be fixedly attached to the members or integral with the members. The hexagonal unit cell exhibits multiple stable states. In addition to the fully expanded and fully contracted states shown in FIGS. 14a and 14b, the hexagonal cell also may attain two intermediate stable configurations in which only one of the two upper side members 762 is collapsed inward along with top member 754.

The above described bistable and multistable cells may be used in any of a variety of medical applications e.g. to form stents, clamps, clips, expander rings or bistable valves, and in non-medical applications as well. For example, the device of the present invention may be used as an anchor for a graft, in which a tubular sleeve comprising a polymeric material is mounted an expandable tube such as depicted in FIGS. 5a and 5b. The graft may comprise a polyurethane material or ePTFE (expanded polytetrafluoroethylene). In addition, individual circumferential rings of unit cells, as described hereinabove, may be used for anchoring a draft, for example, as used in abdominal aortic aneurysm grafts.

Figure 13:
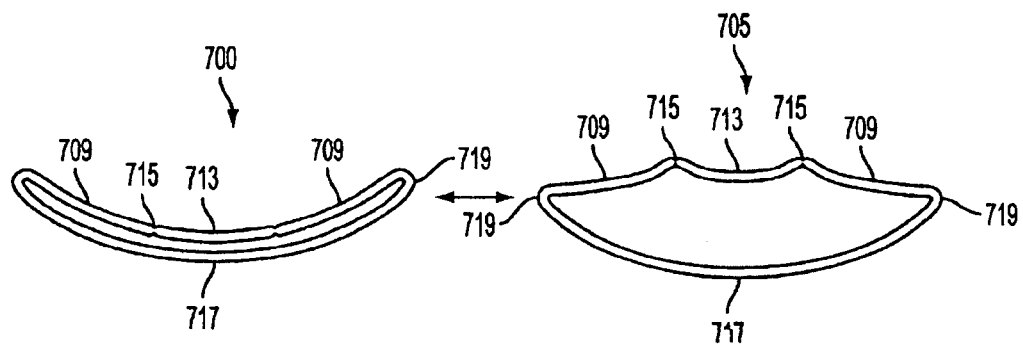
FIGS. 13a and 13b show, respectively a multistable cell in the fully contracted state and in the fully expanded state.
Figure 15:
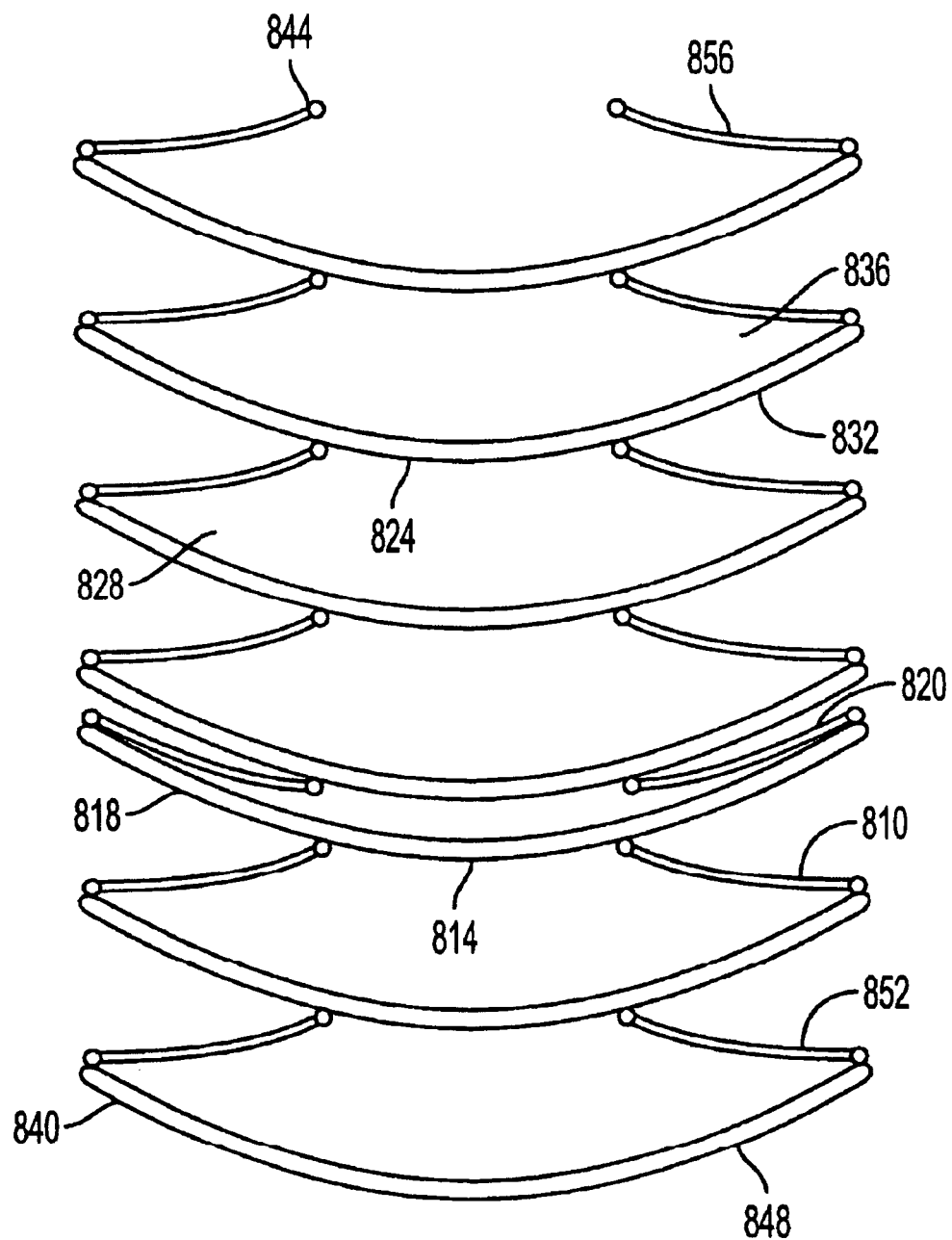
FIG. 15 shows several unit cells as shown in FIGS. 14a,b joined together and in the fully expanded state.

In one such application a ring or stent is formed of the hinged cells of FIGS. 13a and 13b. As shown in FIG. 15, a series of unit cells of the type depicted in FIG. 13 are joined together so that the top member of a cell forms a portion of the bottom member of an adjoining cell. As depicted, top member 814 of cell 810 forms a portion of bottom element 818 of cell 820. Similarly, top member 824 of cell 828 forms a portion of bottom element 832 of cell 836. Although the ring or stent in FIG. 15 has been cut for illustrative purposes, the two ends 840 and 844 are normally joined together with a portion of lower member 848 of cell 852 serving as an upper member for cell 856. The ring so formed has a range of stable states including a fully expanded state and a fully contracted state. Where the individual cells are made identically, only the fully expanded states may be accessed by the application of a uniform radially outward force to the stent in the fully contracted state. It may serve as a clamp or collar, an expansion ring or a stent. Larger stents may be formed by interconnecting a plurality of such rings.

In the described drawings and text only some examples of different embodiments have been provided. While the devices of the present invention may appear to employ unit cells similar to those of previously-known devices, the mechanical results and mode of operation are completely different due to the special combination of a rigid section and a more flexible section in the same unit cell. Of course there are, beside the illustrated sinusoidal shape many other possible basic shapes for the unit cells, with similar characteristic behavior.

While preferred illustrative embodiments of the invention are described above, it will be apparent to one skilled in the art that various changes and modifications may be made therein without departing from the invention. The appended claims are intended to cover all such changes and modifications that fall within the true spirit and scope of the invention.

What is claimed is:

1. An expandable support device comprising:
an expandable tube formed of a plurality of unit cells, each unit cell having a length, at least one unit cell of said plurality of unit cells having a stable contracted configuration and a stable expanded configuration, said at least one unit cell comprising
a rigid segment extending the length of said unit cell, and
a flexible segment extending the length of said unit cell, the flexible segment being more flexible than the rigid segment such that when said unit cell is forcibly expanded in a radially outward direction from the stable contracted configuration toward the stable expanded configuration, said unit cell passes a transition point between the stable contracted configuration and the stable expanded configuration, and once said unit cell passes the transition point, the difference in flexibility between the flexible segment and the rigid segment causes the unit cell to automatically move further toward the expanded configuration.

2. The device of claim 1, wherein the expandable tube comprises a biodegradable material selected from the group consisting of: poly(L-lactide-coglycolide), polyhydroxyalkanoate, polyester amide, a chitosan and genipin structure and a silicon and iron composite.

3. The device of claim 1, wherein the rigid segment is coupled to the flexible segment.

4. The device of claim 1, wherein the flexible segment undergoes rotational motion during expansion.

5. The device of claim 1, wherein the flexible segment is arcuate prior to expansion of the unit cell.

6. The device of claim 1, wherein the plurality of unit cells define a wall having a plurality of slots therethrough with at least a portion of the plurality of slots having a wave-like shape when the device is in the stable contracted configuration.

7. The device of claim 6, wherein the wave-like shape transitions to an expanded wave-like shape when the device is expanded.

8. The device of claim 1, further comprising a tubular sleeve mounted on the plurality of unit cells.

9. The device of claim 8, wherein the tubular sleeve comprises a drug or bioactive agent.

10. The device of claim 1, wherein the flexible segment has a smaller cross-section than the rigid segment.

11. The device of claim 10, wherein the rigid segment remains unflexed during transition of the flexible segment from the stable contracted configuration to the stable expanded configuration.

12. The device of claim 1, wherein the flexible segment is coupled to the rigid segment by plastic hinges.

13. The device of claim 1, wherein the flexible segment is coupled to the rigid segment by elastic hinges.

14. The device of claim 1, wherein the radially outward force is applied by pneumatic, hydraulic, mechanical or electromechanical means.

15. The device of claim 1, wherein the device has a larger diameter in the stable expanded configuration than in the stable contracted configuration.

16. The device of claim 1, wherein one or more of the unit cells have a symmetrical load-displacement characteristic around the transition point.

17. The device of claim 1, wherein one or more of the unit cells have an asymmetrical load-displacement characteristic around the transition point, with the expanded configuration being the more stable configuration.

18. The device of claim 1, wherein one or more of the unit cells have an asymmetrical load-displacement characteristic around the transition point, with the contracted configuration being the more stable configuration.

19. The expandable support device of claim 1, wherein the rigid segment and the flexible segment each have a generally longitudinal wave-like shape, and wherein the rigid segment and the flexible segment are generally in phase when the unit cell is in the stable contracted configuration and generally out of phase when the unit cell is in the stable expanded configuration.

20. The expandable support device of claim 1, wherein the rigid segment and the flexible segment each have an arcuate shape, and at least a first portion of the flexible segment is generally concave when the unit cell is in the stable contracted configuration and at least a portion the flexible segment is generally convex when the unit cell is in the stable expanded configuration.

21. The expandable support device of claim 1, wherein no external influence is required after said unit cell passes the transition point to expand said unit cell from the transition point to the stable expanded configuration.

22. The expandable support device of claim 1, wherein the expandable support device is configured for deployment in a blood vessel.

23. The device of claim 1, wherein the expandable tube is formed at least partially of a biodegradable material.

24. An expandable support device comprising:
an expandable tube formed of a plurality of unit cells, at least one unit cell of said plurality of unit cells having a stable contracted configuration and stable expanded configuration, wherein:
during a first phase of expansion, said at least one unit cell is expanded beyond a transition point by application of a radially outward force to the expandable tube;
during a second phase of expansion that occurs after said unit cell is expanded beyond the transition point, said unit cell automatically expands further toward the stable expanded configuration; and
after the expandable tube is forcibly compressed such that said unit cell is contracted past the transition point, the at least one unit cell is configured to automatically contract further toward the stable contracted configuration.

25. The device of claim 24, wherein the expandable tube comprises a biodegradable material selected from the group consisting of: poly(L-lactide-co-glycolide), polyhydroxyalkanoate, polyester amide, a chitosan and genipin structure and a silicon and iron composite.

26. The device of claim 24, wherein the plurality of unit cells define a wall having a plurality of slots therethrough with at least a portion of the plurality of slots having a wave-like shape when the device is in the stable contracted configuration.

27. The device of claim 24, further comprising a tubular sleeve mounted on the plurality of unit cells.

28. The device of claim 27, wherein the tubular sleeve comprises a drug or bioactive agent.

29. The device of claim 27, wherein no external influence is required after said unit cell passes the transition point to expand said unit cell from the transition point to the stable expanded configuration.

30. The device of claim 24, wherein the expandable tube is formed at least partially of a biodegradable material.

* * * * *